United States Patent
Liu et al.

(10) Patent No.: US 11,324,969 B2
(45) Date of Patent: May 10, 2022

(54) METHOD AND DEVICE FOR FOCUSING X-RAY AND RADIOTHERAPY APPARATUS

(71) Applicants: OUR UNITED CORPORATION, Xi'an (CN); SHENZHEN OUR NEW MEDICAL TECHNOLOGIES DEVELOPMENT, Shenzhen (CN)

(72) Inventors: Haifeng Liu, Xi'an (CN); Xiaoqi Lin, Xi'an (CN); Peng Zan, Xi'an (CN)

(73) Assignees: OUR UNITED CORPORATION, Shaanxi (CN); SHENZHEN OUR NEW MEDICAL TECHNOLOGIES DEVELOPMENT, Guangdon (CN)

( * ) Notice: Subject to any disclaimer, the term of this patent is extended or adjusted under 35 U.S.C. 154(b) by 164 days.

(21) Appl. No.: 16/632,277
(22) PCT Filed: Jun. 7, 2018
(86) PCT No.: PCT/CN2018/090280
§ 371 (c)(1),
(2) Date: Jan. 17, 2020
(87) PCT Pub. No.: WO2019/015412
PCT Pub. Date: Jan. 24, 2019

(65) Prior Publication Data
US 2020/0230436 A1 Jul. 23, 2020

(30) Foreign Application Priority Data
Jul. 19, 2017 (CN) .......................... 201710589635.3

(51) Int. Cl.
*A61N 5/10* (2006.01)
*G21K 1/02* (2006.01)
(52) U.S. Cl.
CPC ............ *A61N 5/1042* (2013.01); *A61N 5/103* (2013.01); *A61N 5/1077* (2013.01); *G21K 1/02* (2013.01); *A61N 2005/1089* (2013.01)

(58) Field of Classification Search
None
See application file for complete search history.

(56) References Cited

U.S. PATENT DOCUMENTS 8,788,017 B2 * 7/2014 Yu .............................. A61B 6/00
600/411
2002/0085674 A1 * 7/2002 Price ........................ H01J 35/00
378/122

(Continued)

FOREIGN PATENT DOCUMENTS

CN        1185981 A        7/1998
CN        1310029 A        8/2001

(Continued)

OTHER PUBLICATIONS

International search report of PCT application No. PCT/CN2018/090280 dated Aug. 23, 2018.

(Continued)

*Primary Examiner* — Edwin C Gunberg
(74) *Attorney, Agent, or Firm* — Knobbe Martens Olson & Bear LLP (57) ABSTRACT

A method for focusing an X-ray method is provided and the method includes: emitting an electron beam by an electron beam generator; shooting the electron beam onto a target to generate an X-ray beam; and causing the X-ray beam to pass through each collimating channel of a same collimating channel group of a collimator to focus on a focus of the collimating channel group. The collimator includes at least one collimating channel group. Each collimating channel group includes at least two collimating channels. The same collimating channel group has one focus or a plurality of focuses.

20 Claims, 9 Drawing Sheets

(56) References Cited

U.S. PATENT DOCUMENTS

| | | | |
|---|---|---|---|
| 2002/0106055 A1* | 8/2002 | Cash | G21K 1/06 |
| | | | 378/65 |
| 2004/0006254 A1* | 1/2004 | Weil | A61N 5/10 |
| | | | 600/2 |
| 2004/0037393 A1 | 2/2004 | Birdwell et al. | |
| 2010/0034352 A1 | 2/2010 | Aoi et al. | |

FOREIGN PATENT DOCUMENTS

| | | |
|---|---|---|
| CN | 101642605 A | 2/2010 |
| CN | 203408368 U | 1/2014 |
| CN | 107456663 A | 12/2017 |
| JP | H0639045 A | 2/1994 |

OTHER PUBLICATIONS

First office action of Chinese application No. 201710589635.3 dated Sep. 19, 2018.
Second office action of Chinese application No. 201710589635.3 dated Apr. 30, 2019.
Third office action of Chinese application No. 201710589635.3 dated Jul. 19, 2019.
Fourth office action of Chinese application No. 201710589635.3 dated Nov. 8, 2019.

* cited by examiner

METHOD AND DEVICE FOR FOCUSING X-RAY AND RADIOTHERAPY APPARATUS

This application is a 371 of PCT international patent application No.: PCT/CN2018/090280 filed on Jun. 7, 2018, which claims priority to Chinese Patent Application No. 201710589635.3, filed on Jul. 19, 2017 and entitled "X-RAY FOCUSING METHOD AND DEVICE AND RADIOTHERAPY APPARATUS", the entire contents of which are incorporated herein by reference.

TECHNICAL FIELD

The present disclosure relates to the field of medical instrument technology, and in particular to a method and device for focusing an X-ray and a radiotherapy apparatus.

BACKGROUND

Figure 1:
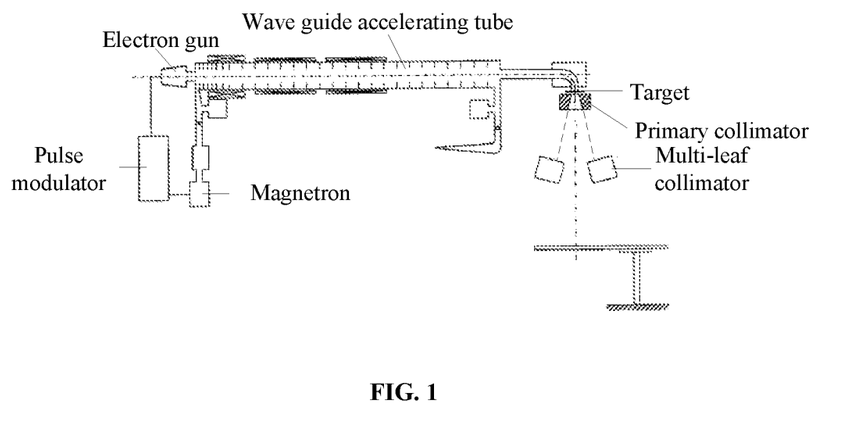
FIG. 1 is a schematic structural view of a conventional accelerator.

Radiotherapy is a main means for tumor treatment. A conventional radiotherapy apparatus includes a gamma knife and an accelerator. The gamma knife emits radioactive rays using a natural radioisotope (generally emits a y ray using Co-60) for radiotherapy of human tumors. As shown in FIG. 1, the accelerator generally includes a pulse modulator, an electron gun, a magnetron, a waveguide accelerating tube and a target. The pulse modulator is generally used to form a high-voltage pulse. The electron gun emits an electron beam with certain energy and beam current, as well as a certain velocity and angle. The magnetron forms a high-power microwave to control the direction of an electron. Then, the electron is accelerated by the waveguide accelerating tube. The accelerated electron is shot onto the target to form a conical ray (generally, an X-ray).

Figure 2:
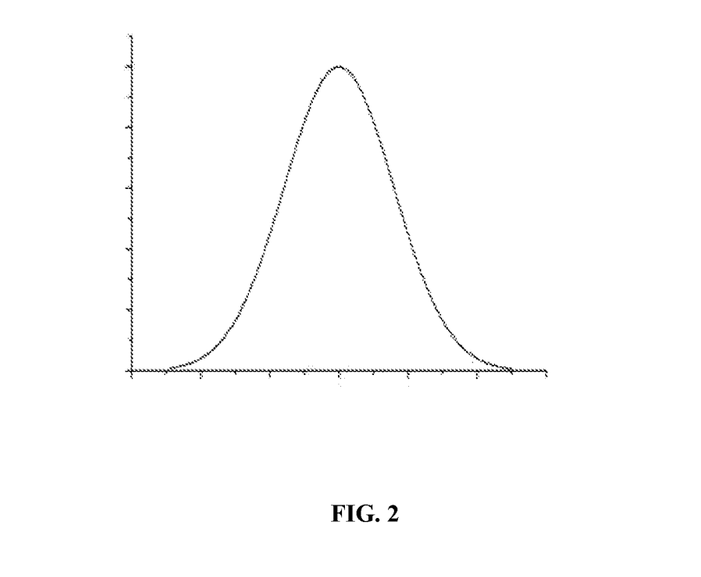
FIG. 2 is a schematic diagram of dose distribution of X-rays generated by an accelerator.

As shown in FIG. 1, since the ray generated by the accelerator is a cone beam of which dose distribution is as shown in Gaussian distribution of FIG. 2. That is, an intermediate region of the ray is high in dose, and a peripheral region is low in dose. It is generally necessary to re-beam a high-dose ray beam by a primary collimator and to perform conformal processing on the intermediate region by a multi-leaf collimator so as to satisfy a high-dose requirement of tumor treatment.

Therefore, the conventional accelerators are all used for conformal treatment. That is, a beam passing region of which the shape is similar to that of a tumor is formed by the multi-leaf collimator, such that the shape of a beam passing through a human body coincides with the shape of the tumor. Clinically, a conformal therapy is mainly applicable to relatively larger tumors while the gamma knife is generally used for focused treatment of relatively smaller tumors.

SUMMARY

Embodiments of the present disclosure provide a method and device for focusing an X-ray and a radiotherapy apparatus, which can form a focused treatment by an X-ray beam generated via an accelerator.

To fulfil the above objective, the embodiments of the present disclosure adopt the following technical solutions.

In a first aspect, an embodiment of the present disclosure provides a method for focusing an X-ray, including:

emitting an electron beam by an electron beam generator;
shooting the electron beam onto a target to generate an X-ray beam; and
causing the X-ray beam to pass through each collimating channel of a same collimating channel group of a collimator to focus on a focus of the collimating channel group. The collimator includes at least one collimating channel group. Each collimating channel group includes at least two collimating channels. The same collimating channel group has one focus or a plurality of focuses.

In a second aspect, an embodiment of the present disclosure provides a device for focusing an X-ray, including:

an electron beam generator, configured to emit an electron beam;
a target; and
a collimator;
wherein the electron beam is shot on the target and an X-ray beam may be generated; and the collimator includes at least one collimating channel group, each collimating channel group includes at least two collimating channels, and the same collimating channel group has one focus or a plurality of focuses.

In a third aspect, an embodiment of the present disclosure provides a radiotherapy apparatus, including any of the X-ray focusing devices provided by the present disclosure.

The embodiments of the present disclosure provide the method and device for focusing an X-ray and the radiotherapy apparatus. The electron beam generator emits the electron beam. The electron beam is shot onto the target to generate the X-ray beam. The X-ray beam passes through the collimator to focus on one focus or a plurality of focuses so as to realize focusing. The X-ray focusing device may be applied to the radiotherapy apparatus. A focus point corresponds to a position of a patient's tumor, such that the tumor can be killed by X-rays for the purpose of treatment. Compared with a conventional device that uses X-rays for a conformal treatment, the X-ray focusing device provided by the present disclosure can perform a focused treatment and the focus point may be different based on the sizes of the collimating channels. Compared with the conformal treatment, a subtler treatment can be realized and a better treatment effect to small tumors in the early stage of a disease can be obtained. Moreover, the focused treatment uses low-energy X rays to focus on the target, such that a high-dose requirement on the target is satisfied during radiotherapy.

BRIEF DESCRIPTION OF THE DRAWINGS

In order to describe the technical solutions in the embodiments of the present or the prior art more clearly, the following briefly introduces the accompanying drawings required for describing the embodiments or the prior art. Apparently, the accompanying drawings in the following description show merely some embodiments of the present disclosure, and a person of ordinary skill in the art may also derive other drawings from these accompanying drawings without creative efforts.

Reference numbers in the drawings are described as below:

1: electron beam generator; 2: electron beam; 3: target; 4: X-ray beam; 5: collimator; 6: beam-splitting component.

DETAILED DESCRIPTION

The technical solutions in the embodiments of the present disclosure will be clearly described below in its entirety with reference to the accompanying drawings in the embodiments of the present disclosure. It is obvious that the described embodiments are only part but not all of the embodiments of the present disclosure. All other embodiments obtained by those of ordinary skill in the art based on the embodiments of the present disclosure without paying any creative labor are within the scope of protection of the present disclosure.

Figure 3:
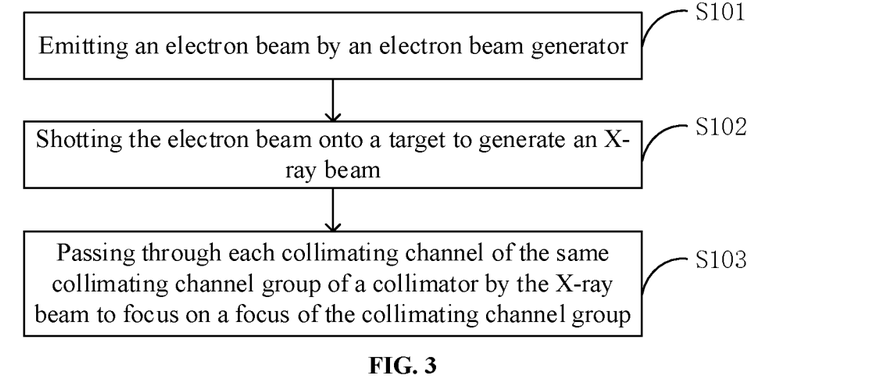
FIG. 3 is a schematic diagram of a method for focusing an X-ray in accordance with the present disclosure.
Figure 4:
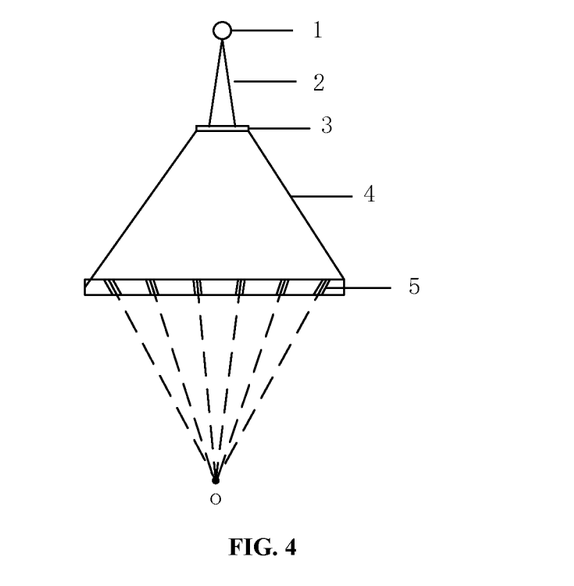
FIG. 4 is a schematic diagram of an X-ray focusing in accordance with the present disclosure.

The present disclosure provides a method for focusing an X-ray, including the following steps as shown in FIGS. 3 and 4.

In step 101, an electron beam generator 1 emits an electron beam 2. Exemplarily, in order to emit the electron beam, the electron beam generator may include a pulse modulator, an electron gun, a magnetron, a waveguide accelerating tube, etc. A reference may be made to a conventional accelerator for generation and emission of the electron beam by the electron beam generator may be referred to a conventional accelerator, which will not be described in detail herein.

In step 102, the electron beam 2 is shot onto a target 3 to generate an X-ray beam 4. Generally, the target may be formed from metal such as a tantalum plate or a copper plate. When the electron beam is shot onto the target, a collision occurs. At this time, an electron is suddenly slowed down, and its lost kinetic energy will be released in the form of photon to form the X-ray beam.

In step 103, the X-ray beam 4 passes through each collimating channel of the same collimating channel group of a collimator 5 to focus on a focus o of the collimating channel group. The collimator includes at least one collimating channel group. Each collimating channel group includes at least two collimating channels. The same collimating channel group has one or a plurality of focuses.

In the present disclosure, the collimator may be a circular collimator, a bowl-shaped collimator, a rectangular collimator, etc. for head treatment or body treatment. The shape of the collimator will not be limited by the present disclosure. If the collimator is a circular collimator, the at least two collimating channels of the same collimating channel group may be located on the same circle. In the present disclosure, when the radiotherapy apparatus is turned on, the collimating channel groups corresponding to emitted beams may be the same collimating channel group. Certainly, the collimating channels may be classified into the same collimating channel group based on their sizes, shapes, angles, positions, etc. Exemplarily, the collimating channels of the same collimating channel group are the same in size, and the collimating channels of the different collimating channel groups are different in size.

Figure 5:
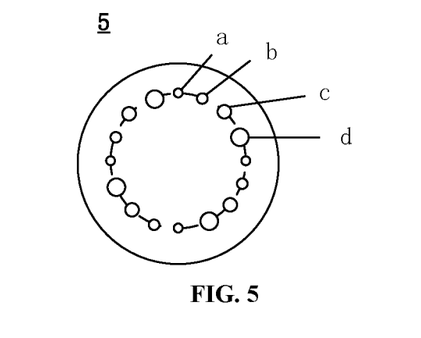
FIG. 5 is a schematic diagram of a circular collimator in accordance with the present disclosure.

Exemplarily, as shown in FIG. 5, four collimating channel groups a, b, c and d are disposed on the circular collimator. Each collimating hole group includes four collimating holes in the same size. Diameters of the collimating hole groups have the following relationship: a<b<c<d. Certainly, settings of a circular or bowl-shaped collimator are not limited to FIG. 5. The present disclosure only takes FIG. 5 for an exemplary illustration.

Figure 6:
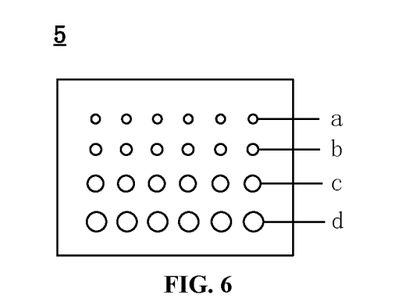
FIG. 6 is a schematic diagram of a rectangular collimator in accordance with the present disclosure.

If the collimator is a rectangular collimator, the collimating channels may be arranged in a matrix. The collimating channels in the same row or line form one collimating channel group. Exemplarily, as shown in FIG. 6, the collimating channels of the collimator are arranged in a matrix, and four collimating channel groups a, b, c and d are included. Each collimating hole group includes 6 collimating channels in the same size. Diameters of the collimating channel groups have the following relationship: a<b<c<d.

Figure 7:
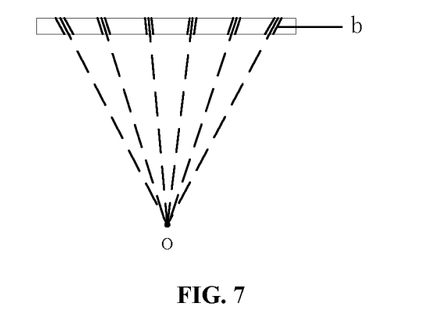
FIG. 7 is a schematic diagram of a focusing section of a collimating channel group in accordance with the present disclosure.

In the present disclosure, the same collimating channel group has one or a plurality of focuses. Exemplarily, the same collimating channel group has one focus. As shown in FIG. 7, taking the collimating channel group b as an example, the collimating channel group b may have one focus. That is, an X-ray may pass through each collimating channel to focus on one focus o. In the present disclosure, the same collimating channel group has one focus, and the X-ray beam passing through the different collimating channel groups has a same focusing position. As shown in FIGS. 5 and 6, if the collimating channel groups a and b are switched, the focus positions of the collimating channel groups are at the position of the focus o. It should be noted that generally, during a radiotherapy, every time the beam passes through one collimating channel group, it cannot focus on the focus until the beam passes through the collimating channels. In the present disclosure, different collimating channel groups have different focuses, but the focus positions of the different collimating channel groups may be the same.

Figure 8:
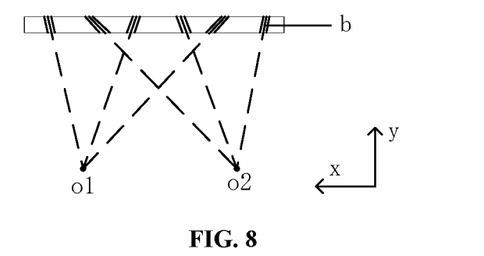
FIG. 8 is a schematic diagram of a focusing section of another collimating channel group in accordance with the present disclosure.
Figure 9:
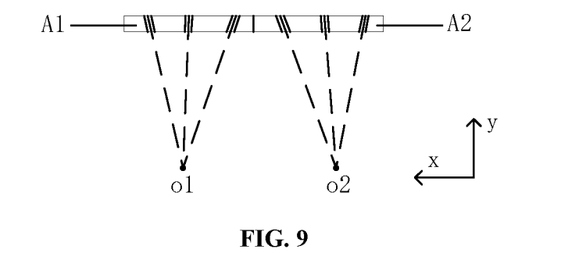
FIG. 9 is a schematic diagram of a focusing section of yet another collimating channel group in accordance with the present disclosure.

Certainly, the same collimating channel group may also have a plurality of focuses, and the focus positions of X-ray beams passing through the same collimating channel group are different. As shown in FIG. 8, taking the collimating channel group b as an example, the collimating channel group b may have two focuses, namely o1 and o2. Exemplarily, the collimator may consist of a plurality of collimator blocks. In the case that the same collimating channel group has a plurality of focuses, the X-ray beam may pass through a collimating channel on each collimator block to focus on one focus, and different collimator blocks have different focuses. Further, different collimator blocks may be provided to adjust sizes and positions of the focuses so as to meet different treatment demands. Exemplarily, as shown in FIG. 9, the collimator includes a collimator block A1 and a collimator block A2, and the collimator block A1 has a focus o1 and the collimator block A2 has a focus o2. In FIGS. 8 and 9, o1 and o2 are at different positions in one direction (e.g., an x direction). It should be noted that o1 and o2 may also be at different positions in two directions (e.g., an x direction and a y direction), or in three directions (e.g., an x direction, a y direction and a z direction). Certainly, the shapes of collimating hole groups may be different, which will not be limited by the present disclosure. Described above are merely taken as an example for illustration.

In the present disclosure, the collimating channel may be for example circular and may have a diameter ranging from 2 mm to 20 mm, e.g., 2 mm, 4 mm, 6 mm, 8 mm, 12 mm, 14 mm, 16 mm and 18 mm. The collimating channels are applied to the radiotherapy apparatus suitable for treating relatively small head tumors. Certainly, the diameters of the collimating channels may also range from 20 mm to 200 mm, such that a focus point is bigger. Thus, the radiotherapy apparatus may be suitable for treating relatively big body tumors.

In addition, in the present disclosure, the X-ray beam 4 passes through each collimating channel of the same collimating channel group of the collimator 5 to focus on the focus o of the collimating channel group. The X-ray beam 4 may also sequentially pass through each collimating channel of the same collimating channel group of the collimator, and the beam that passes through each collimating channel group passes through the focus o and thus focusing on the focus o of the collimating channel group is realized.

According to the method for focusing an X-ray provided by the present disclosure, the electron beam generator emits the electron beam. The electron beam is shot onto the target to generate the X-ray beam. The X-ray beam passes through the collimator to focus on one focus or a plurality of focuses to realize focusing. The X-ray focusing device may be applied to the radiotherapy apparatus. The focus point corresponds to a position of a patient's tumor, such that the tumor can be killed by X-rays for the purpose of treatment. Compared with a conventional device that uses X-rays for a conformal treatment, the X-ray focusing device provided by the present disclosure can perform a focused treatment. The focused treatment uses low-energy X rays to focus on the target, such that a dose rate at the focus can be increased and a high-dose requirement on the target can be satisfied during a radiotherapy. Compared with the conformal treatment, a subtler treatment can be realized and a better treatment effect to small tumors in the early stage of a disease can be obtained.

According to the method for focusing an X-ray provided by the present disclosure, the collimating channels of the same collimating channel group may be the same in size, and the collimating channels of the different collimating channel groups are different in size. Taking the collimator shown in FIGS. 5 and 6 as an example, the X-ray beam passing through the same collimating channel group focuses on the focus. The X-ray beam passes through the collimating channels of the different collimating channel groups by switching, such that rays of different sizes are switched.

According to the method for focusing an X-ray provided by the present disclosure, the electron beam is a divergent beam. That is, the electron beam may be a broad beam, and a broad-beam shooting is performed when the electron beam contacts the target, such that a contact area between the electron beam and the target is increased. With respect to a narrow-beam shooting of a conventional electron beam, X-rays can be generated within a wider range. The X-rays pass through the collimator to focus on the focus, such that a high dose of the focus can be realized while a skin dose of a human body is diverged and reduced.

Figure 10:
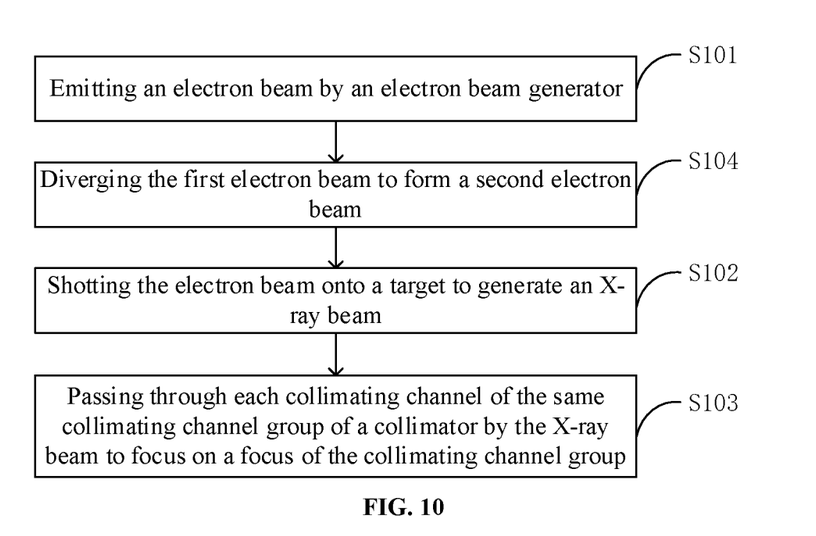
FIG. 10 is a schematic diagram of another method for focusing an X-ray in accordance with the present disclosure.

Alternatively, as shown in FIG. 10, the electron beam generator emits a first electron beam which is a narrow beam. Exemplarily, the first electron beam may be a beam with a beam width not more than 5 mm. Before step 102, the method further includes the following step.

In step 104, the first electron beam is diverged to form a second electron beam. The second electron beam is a divergent beam. A broad-beam shooting is performed when the second electron beam contacts the target, such that a contact area between the electron beam and the target is increased. With respect to a narrow-beam shooting of a conventional electron beam, X-rays can be generated within a wider range. The X-rays pass through the collimator to focus on the focus, such that a high dose of the focus can be realized while a skin dose of a human body is diverged and reduced.

Figure 11:
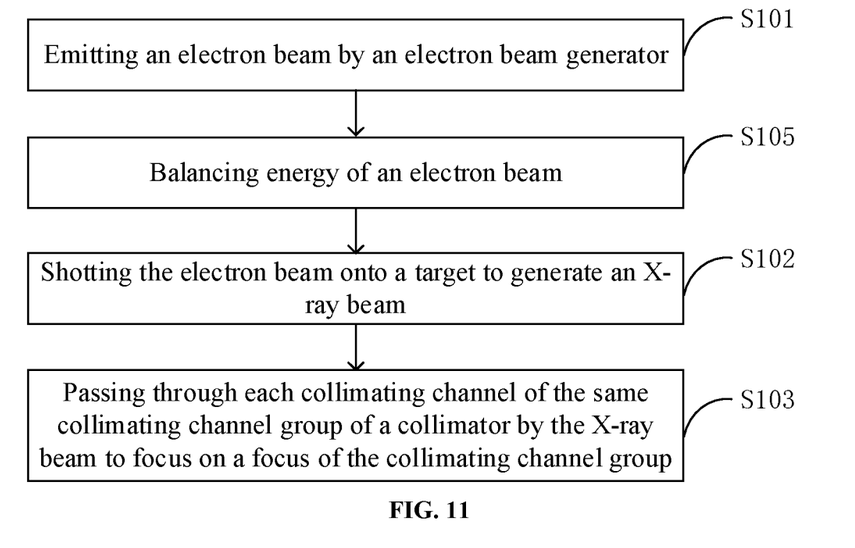
FIG. 11 is a schematic diagram of yet another method for focusing an X-ray in accordance with the present disclosure.

The present disclosure provides another focusing method, including the following steps as shown in FIG. 11.

In step 105, energy of an electron beam is balanced, such that energy of a contact surface between the electron beam and the target is balanced. Exemplarily, a flattening filter may be disposed between an electron beam generator and a target and configured to balance energy of the electron beam, such that energy of the contact surface between the electron beam and the target is balanced.

Exemplarily, the present disclosure provides yet another focusing method, in which energy of an X-ray beam may be balanced. Exemplarily, a flattening filter, etc. may be disposed below a target or above a collimator to balance energy of the X-ray beam.

According to the method for focusing an X-ray provided by the present disclosure, by balancing energy of the electron beam or the X-ray beam, an energy size of the X-ray beam can be more balanced, and energy distribution of the X-ray beam can meet a certain relationship. For example, an intermediate region is relatively low in energy and a peripheral region is relatively high in energy to facilitate increasing of the dose of a target. Certainly, a balance of energy of rays can also be realized by the target. For example, it may be set that the intermediate region of the target is low in density and the peripheral region is high in density, such that the dose rate of the shot X-ray beam after shooting is low in middle and is high on two sides.

According to the focusing method provided by the present disclosure, that the X-ray beam passes through each collimating channel of the same collimating channel group of a collimator includes: the X-ray beam sequentially passes through each collimating channel of the same collimating channel group of a collimator. Exemplarily, the electron beam may be moved together with the target, such that X-ray beams are emitted at different positions, and the X-ray beams sequentially pass through each collimating channel of the same collimating channel group of the collimator. In this way, the X-ray beam passes through one collimating channel at a time, such that the dose of the X-ray beam passing through each collimating channel is relatively large, and the dose rate of the focus is increased to satisfy a high-dose requirement of a radiotherapy. Exemplarily, as shown in FIGS. 5, 6 and 7, the X-ray beam sequentially passes through each collimating channel in the collimating channel group b. Since the X-ray beam passing through each collimating channel passes through the focus o, a scanning type of focusing is realized.

Certainly, it may also by moving the electron beam to change a shooting position of the electron beam on the target, such that the position of the X-ray beam changes, and the X-ray beam sequentially passes through each collimating channel of the same collimating channel group of the collimator. Alternatively, it may also by moving both the electron beam and the target to change the position of the X-ray beam, such that the X-ray beam sequentially passes through each collimating channel of the same collimating channel group of the collimator.

Exemplarily, according to the focusing method provided by the present disclosure, that the electron beam is shot onto the target to generate the X-ray beam includes: the electron beam is moved to change the shooting position of the electron beam on the target and to generate an X-ray beam at each shot position of the target. Exemplarily, the target may be shaped like a bowl. The electron beam is shot onto different positions of the target to respectively generate one X-ray beam at each position. The X-ray beam in each position passes through the collimating channels of the same collimating channel group to focus on the focus. Thus, the X-ray beam passes through one collimating channel at a time, and the dose of the X-ray beam passing through each collimating channel is relatively large. Therefore, the dose rate of the focus can be increased to satisfy the high-dose requirement of a radiotherapy.

Figure 12:
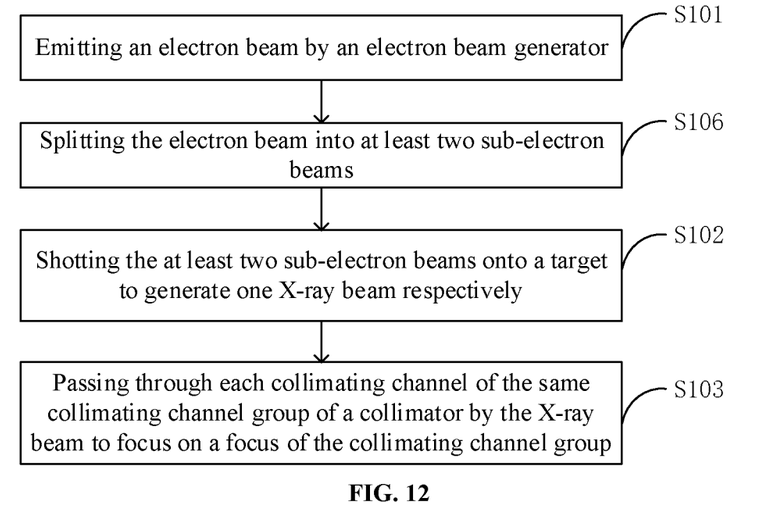
FIG. 12 is a schematic diagram of yet another method for focusing an X-ray in accordance with the present disclosure.
Figure 13:
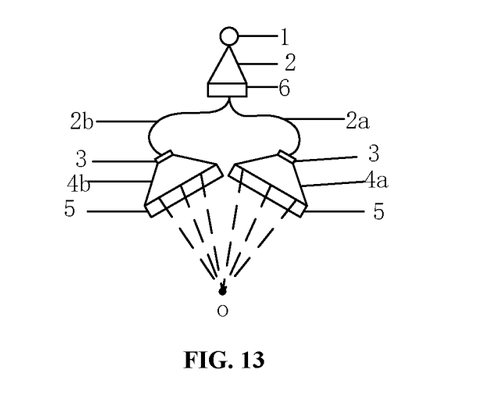
FIG. 13 is a schematic diagram of an X-ray focusing in accordance with the present disclosure.

Exemplarily, the present disclosure provides a focusing method, including the following steps as shown in FIGS. 12 and 13.

In step 101, an electron beam generator 1 emits an electron beam 2.

In step 106, the electron beam is split into at least two sub-electron beams. As shown in FIG. 13, that the electron beam is split by a beam splitting component 6 into two sub-electron beams is taken as an example. Certainly, a beam splitting mode of the electron beam is not limited to the above.

In step 102, the at least two sub-electron beams are shot onto a target to generate one X-ray beam respectively, namely, an X-ray beam 4a and an X-ray beam 4b.

In step 103, each X-ray beam passes through each collimating channel of the same collimating channel group of a collimator to focus on a focus of the collimating channel group.

It should be noted that in FIG. 13, the target 3 may be integrated or may be two separate parts. Similarly, the collimator 5 may be integrated or may be two separated collimator blocks. It should be further noted that FIG. 13 takes that the X-ray beam 4a and the X-ray beam 4b pass through each collimating channel of the collimating channel group to focus on a focus o as an example. Certainly, the X-ray beam 4a and the X-ray beam 4b may respectively focus on two or a plurality of focuses after passing through the collimating channel group of the collimator. In one implementation mode of the present disclosure, the X-ray beam 4a and the X-ray beam 4b may respectively focus on two focus points at different positions after passing through the collimating channel group of the collimator.

The present disclosure provides yet another focusing method, in which the two sub-electron beams are moved to change their shooting positions on the target. For example, the target may be a disk, the two sub-electron beams are moved circumferentially and are caused to rotate circumferentially, and a line connecting the shooting positions on the target forms a circle. Alternatively, the two electron beams are moved horizontally in one or two directions, such that the shooting positions on the target may be arranged in a matrix. It should be noted that in this case, the X-ray generated after each shooting on the target may sequentially pass through each collimating channel of the same collimating channel of the collimator 5, and passes through the focus o of the collimating channel group every time to focus on the focus o of the collimating channel group so as to realize the scanning type of focusing. Certainly, the X-ray generated by each shooting on the target may also pass through a plurality of collimating channels of the same collimating channel group of the collimator, and passes through the focus of the collimating channels every time to focus on the focus o of the collimating channel group. In this way, the X-ray passes through one collimating channel at a time. Thus, the X-ray passing through each collimating channel is relatively large in dose. Further, the dose rate of the focus can be increased to satisfy a high-dose requirement of a radiotherapy.

The present disclosure provides yet another focusing method, in which an electron beam generator emits one electron beam.

That the electron beam is shot onto a target to generate an X-ray beam includes: one electron beam is shot onto a target to generate one X-ray beam. The one X-ray beam may pass through each collimating channel of the same collimating channel group of the collimator to focus on a focus of the collimating channel group. Alternatively, the one X-ray beam may sequentially pass through each collimating channel of the same collimating channel group of the collimator to focus on a focus of the collimating channel group.

Figure 14:
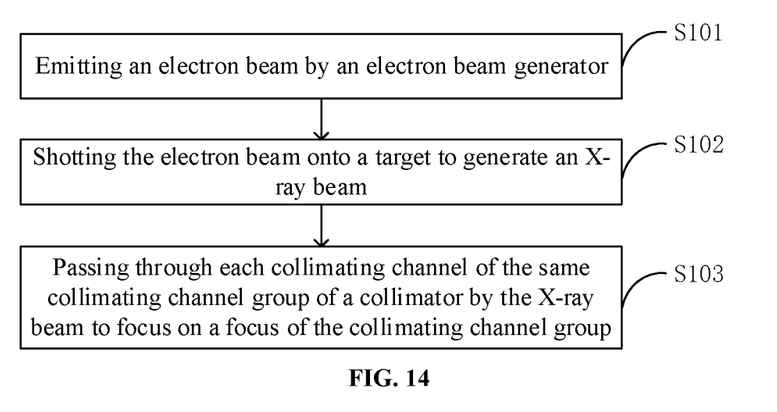
FIG. 14 is a schematic diagram of yet another method for focusing an X-ray in accordance with the present disclosure.

Exemplarily, the present disclosure provides yet another focusing method, including the following steps as shown in FIG. 14.

In step 101, an electron beam generator emits one electron beam. Preferably, the one electron beam is a broad beam in surface contact with a target to reduce energy loss of shooting as much as possible. Certainly, the electron beam may also be a narrow beam.

In step 102, the one electron beam is shot onto the target to generate one X-ray beam.

In step 103, the one electron beam sequentially passes through each collimating channel of the same collimating channel group of the collimator and passes through a focus of the collimating channel group.

It should be noted: the step that the X-ray beam sequentially passes through each collimating channel of the same collimating channel group of the collimator may be implemented by sequentially moving the electron beam to be shot at different positions of the target, shooting onto the target by the electron beam generator, moving the electron beam generator and the target together, or the like. The specific implementation mode will not be limited by the present disclosure, and the above two implementation modes are only taken as examples for explanation.

The embodiment shown in FIG. 14 differs from the embodiment shown in FIG. 12 in that there is one electron beam in the embodiment shown in FIG. 14, and the ray sequentially passes through the collimating channels by moving; and the electron beam is split into two sub-electron beams in the embodiment shown in FIG. 12, and each sub-electron beam is moved to make the ray to sequentially pass through the collimating channels. Certainly, the specific embodiment of moving the electron beam for realizing the focusing is not limited to the above. The present disclosure only takes the above embodiment as an example for explanation.

Exemplarily, the X-ray beam may move circumferentially or horizontally to sequentially pass through each collimating channel of the same collimating channel group of the collimator. Certainly, the horizontal movement may be in a plurality of directions, which will not be limited in detail by the present disclosure.

Figure 15:
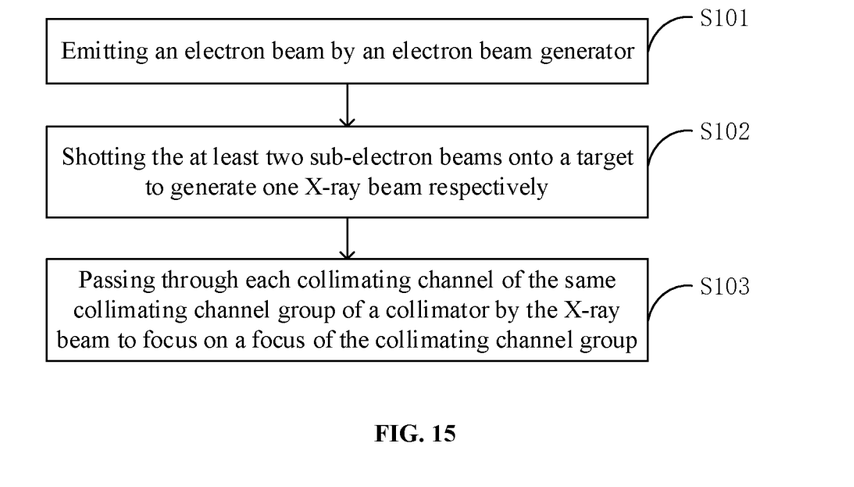
FIG. 15 is a schematic diagram of yet another method for focusing an X-ray in accordance with the present disclosure.
Figure 16:
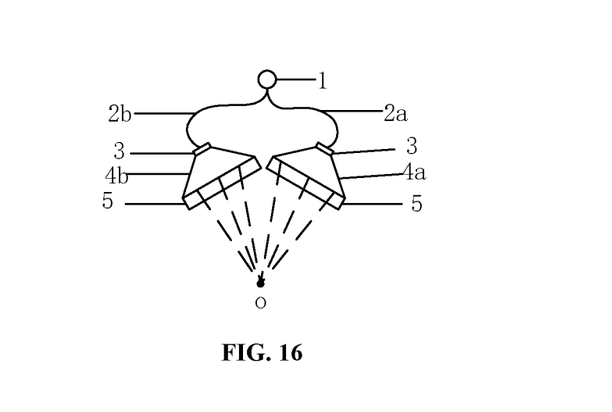
FIG. 16 is a schematic diagram showing X-ray focusing in accordance with the present disclosure.

The present disclosure provides yet another focusing method, including the following steps as shown in FIGS. 15 and 16.

In step 101, an electron beam generator 1 emits at least two electron beams (namely, an electron beam 2a and an electron beam 2b). Exemplarily, there may be a plurality of electron beam generators, and each electron beam generator emits one electron beam. It should be noted that the way in which the electron beam generator emits the at least two electron beams is not limited in detail, and the description is only taken as an example for explanation.

In step 102, the at least two electron beams (namely, the electron beam 2a and the electron beam 2b) are shot onto the target 3 to generate one X-ray beam respectively (namely, an X-ray beam 4a and an X-ray beam 4b). Each X-ray beam passes through each collimating channel of the same collimating channel group of the collimator. That is, the X-ray beam 4a and the X-ray beam 4b pass through each collimating channel of the collimating channel group to focus on a focus o of the collimating channel group.

It should be noted that in the embodiment shown in FIG. 16, the target 3 may be integrated or may be two separate parts. Similarly, the collimator 5 may be integrated an integral whole or may be two separated collimator blocks. It should be further noted that FIG. 16 takes that the X-ray beam 4a and the X-ray beam 4b pass through each collimating channel of the collimating channel group to focus on a focus o as an example. Certainly, the X-ray beam 4a and the X-ray beam 4b may respectively focus on two or a plurality of focuses after passing through the collimating channel group of the collimator. That is, the X-ray beams focus at different positions. In one implementation mode of the present disclosure, the X-ray beam 4a and the X-ray beam 4b may respectively focus on two focuses at different positions after passing through the collimating channel group of the collimator.

Exemplarily, in the embodiment shown in FIGS. 15 and 16, the X-ray beam may be moved to sequentially pass through the collimating channel and to focus on the focus o of the collimating channel group. It should be noted: the step that the X-ray beam sequentially passes through each collimating channel of the same collimating channel group of the collimator may be implemented by sequentially moving the electron beam to be shot at different positions of the target, or shooting onto the target by the electron beam generator, or integrally moving the electron beam generator and the target, or the like. The specific implementation mode will not be limited by the present disclosure, and the above two implementation modes are only taken as examples for explanation. Exemplarily, the X-ray beam may move circumferentially or horizontally to sequentially pass through each collimating channel of the same collimating channel group of the collimator. Certainly, the horizontal movement may be a movement in a plurality of directions, which will not be limited in detail by the present disclosure.

In addition, in the focusing method shown in FIGS. 15 and 16, at least two electron beams are shot onto the target to generate one X-ray beam respectively. A plurality of X-ray beams may pass through the same collimating channel group to focus on focuses at different positions. The collimating channels of the collimating channel group through which each X-ray beam passes may be different in size. Exemplarily, the collimator may include a collimator A1 with a focus of and a collimator A2 with a focus o2. The collimating channels on the collimator block A1 and the collimator block A2 may be different in size. But collimating channel groups of the collimator A1 and the collimator A2 belong to the same collimating channel group if they are located in the same row.

The present disclosure provides yet another focusing method, in which an incident extension line of the electron beam during target shooting forms an angle of 0 to 90° with a central axis of the collimating channel. Thus, the angle formed between the electron beam and the central axis of the collimating channel is reduced. Further, loss of energy can be reduced as much as possible.

The present disclosure provides yet another focusing method, in which the electron beam is perpendicularly incident onto a target surface, such that loss of energy, caused after the electron beam is shot onto the target surface, is reduced. Preferably, the electron beam and an extension line of collimating channel are on the same straight line.

It should be noted that the present disclosure provides an X-ray focusing device corresponding to the method for focusing an X-ray provided by the present disclosure. Therefore, it may refer to the descriptions in the foregoing focusing method for explanations of components in the X-ray focusing device, which will not be explained or repeated in detail below.

Figure 17:
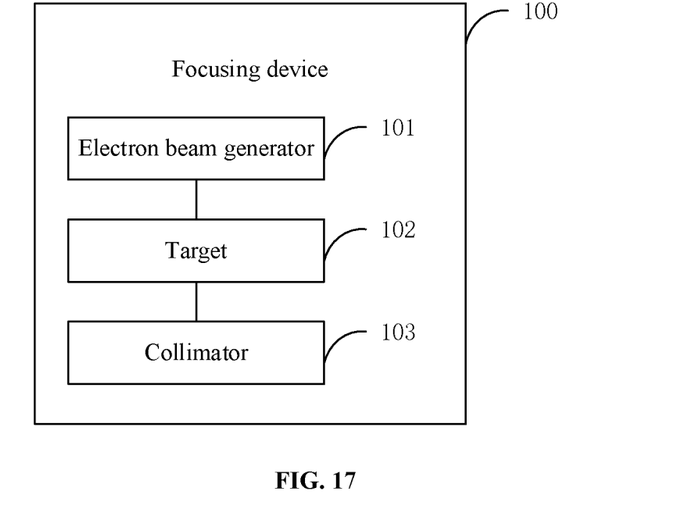
FIG. 17 is a schematic diagram of a focusing device in accordance with the present disclosure.

The present disclosure provides an X-ray focusing device 100, including the following components as shown in FIG. 17.

An electron beam generator 101 is configured to emit an electron beam. In order to emit the electron beam, the electron beam generator may include a pulse modulator, an electron gun, a magnetron, a waveguide accelerating tube, etc. A reference may be made to a conventional accelerator for generation of the electron beam by the electron beam generator, which will not be explained in detail herein.

A target 102, wherein the electron beam is shot on the target and an X-ray beam may be generated. The target may be formed from metal such as a tantalum plate or a copper plate. When the electron beam is shot onto the target, a collision occurs. At this time, an electron is suddenly slowed down, and its lost kinetic energy will be released in the form of photon to form an X-ray beam.

A collimator 103 includes at least one collimating channel group. Each collimating channel group includes at least two collimating channels. The same collimating channel group has one or a plurality of focuses. In the present disclosure, the collimator may be a circular collimator, a bowl-shaped collimator, a rectangular collimator, etc., which will not be limited by the present disclosure. As shown in FIG. 5, if the collimator is a circular collimator, the at least two collimating channels of the same collimating channel group may be located on the same circle, or the plurality of collimating channel groups may be disposed concentrically. As shown in FIG. 6, if the collimator is a rectangular collimator, the collimating channels may be disposed in a matrix, and the collimating channels in the same row or line form one collimating channel group. In the present disclosure, the collimating channels may be classified into the same collimating channel group based on their sizes, shapes, positions, etc. Exemplarily, in the present disclosure, the collimating channels of the same collimating channel group are the same in size, and the collimating channels of the different collimating channel groups are different in size.

In the present disclosure, the same collimating channel group has one or a plurality of focuses. Exemplarily, the same collimating channel group has one focus. As shown in FIG. 7, taking the collimating channel group b as an example, the collimating channel group b may have one focus. That is, an X-ray may pass through each collimating channel to focus on one focus o. In the present disclosure, the same collimating channel group has one focus, and the X-ray passing through the different collimating channel groups has a same focusing position. As shown in FIGS. 5 and 6, the collimating channel groups a and b are switched, and the focus positions of the collimating channel groups are at the position of the focus o. It should be noted that generally, during a radiotherapy, the beam passes through one collimating channel group each time, and it cannot focus on the focus until the beam passes through the collimating channels. In the present disclosure, different collimating channel groups have different focuses, but the focus positions of the different collimating channel groups may be the same.

Certainly, the same collimating channel group may also have a plurality of focuses, and positions of the plurality of focuses are different. Exemplarily, in the present disclosure, the collimator may consist of a plurality of collimating blocks. In the case that the same collimating channel group has a plurality of focuses, center extension lines of the collimating channels on each collimator block may focus on one focus, and different collimator blocks have different focuses.

In the present disclosure, the collimating channels may be for example circular, may have a diameter ranging from 2 mm to 20 mm, e.g., 2 mm, 4 mm, 6 mm, 8 mm, 12 mm, 14 mm, 16 mm and 18 mm, and may be applied to the radiotherapy apparatus suitable for treating relatively small tumors. Certainly, the collimating channels may have diameters ranging from 20 mm to 200 mm to achieve a larger focus point, and thus the radiotherapy apparatus may be suitable for treating relatively bigger tumors.

According to the X-ray focusing device provided by the present disclosure, the electron beam generator emits the electron beam. The electron beam is shot onto the target to generate the X-ray beam. The X-ray beam passes through the collimator to focus on one focus or a plurality of focuses to realize focusing. The X-ray focusing device may be applied to the radiotherapy apparatus. A focus point corresponds to a position of a patient's tumor, such that the tumor can be killed by X-rays for the purpose of treatment. Compared with a conventional device that uses X-rays for a conformal treatment, the X-ray focusing device provided by the present disclosure can perform a focused treatment. The focus point may be different based on the sizes of the collimating channels. Compared with the conformal treatment, a subtler treatment can be realized and a better treatment effect to small tumors in the early stage of a disease can be obtained. The focused treatment uses low-energy X-rays to focus on the target, such that a high-dose requirement on the target is satisfied during a radiotherapy.

According to the method for focusing an X-ray provided by the present disclosure, the collimating channels of the same collimating channel group may be the same in size, and the collimating channels of the different collimating channel groups are different in size. Taking the collimator shown in FIGS. 5 and 6 as an example, the X-ray beam passing through the same collimating channel group focuses on the focus. The X-ray beam passes through the collimating channels of the different collimating channel groups by switching, such that rays of different sizes are switched.

Figure 18:
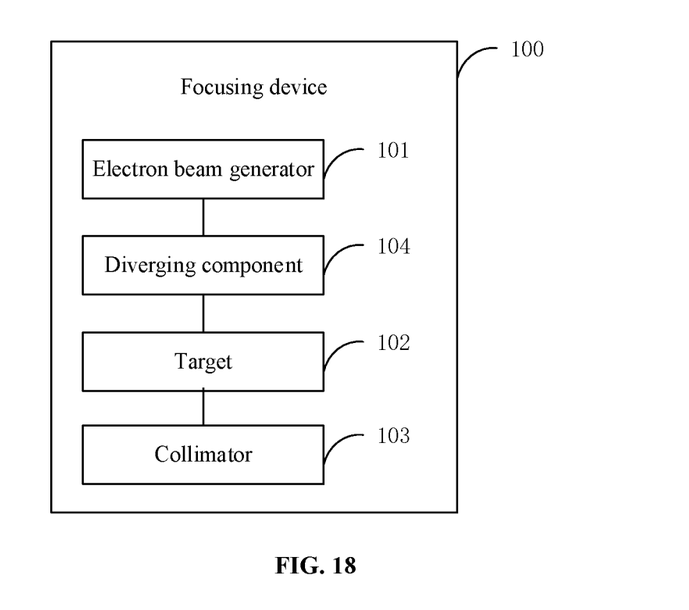
FIG. 18 is a schematic diagram of another focusing device in accordance with the present disclosure.

According to the focusing device provided by the present disclosure, the electron beam is a divergent beam. Alternatively, as shown in FIG. 18, the focusing device further includes a diverging component 104, configured to diverge the electron beam before the electron beam is shot onto the target. In the present disclosure, the electron beam is diverged into the divergent beam, such that the electron beam is in surface contact with the target when shot onto the target.

Figure 19:
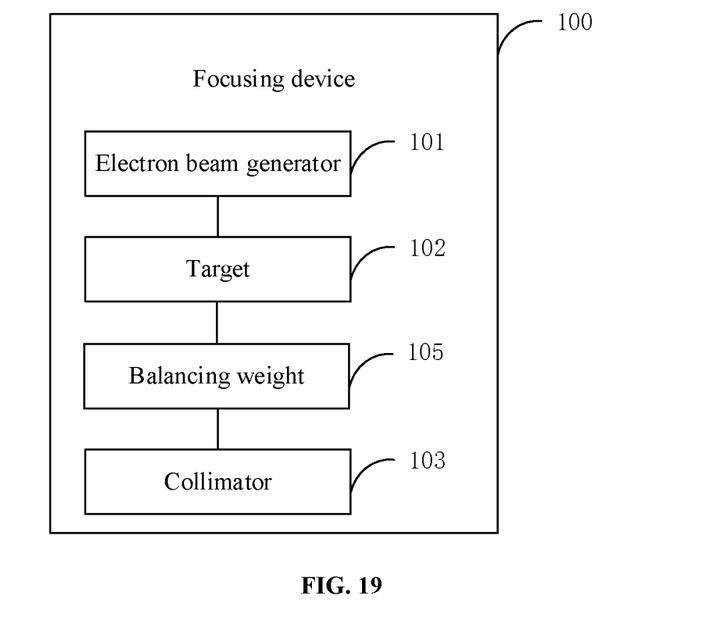
FIG. 19 is a schematic diagram of yet another focusing device in accordance with the present disclosure.

As shown in FIG. 19, the focusing device provided by the present disclosure further includes a flattening filter 105 configured to balance energy of the electron beam and/or the X-ray beam. Exemplarily, a flattening filter may be disposed below the target or above the collimator to balance energy of the X-ray beam.

In the present disclosure, by balancing energy of the electron beam or the X-ray beam, an energy size of the X-ray beam can be more balanced, and energy distribution of the X-ray beam can meet a certain relationship. For example, an intermediate region is relatively low in energy and a peripheral region is relatively high in energy to facilitate increasing of the dose of a target spot. Certainly, a balance of energy of rays can also be realized by the target. For example, it may be set that the intermediate region of the target is relatively low in density, and the peripheral region is high in density, such that the dose rate of the shot X-ray beam is low in middle and high on two sides.

Certainly, a flattening filter may also be disposed between the electron beam generator and the target and configured to balance energy of the electron beam, such that energy of the contact surface between the electron beam and the target is balanced.

Figure 20:
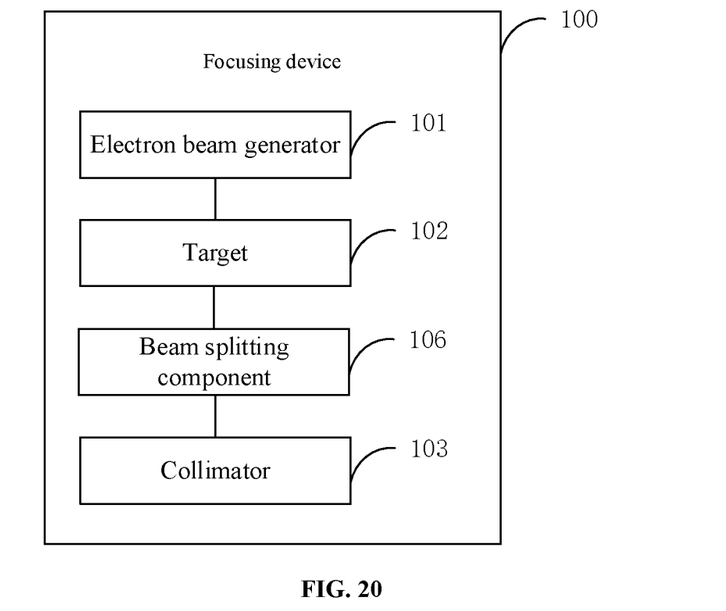
FIG. 20 is a schematic diagram of yet another focusing device in accordance with the present disclosure.

As shown in FIG. 20, the focusing device provided by the present disclosure further includes a beam splitting component 106 configured to split the electron beam into at least two sub-electron beams. Exemplarily, a reference may be made to FIGS. 12 and 13 and their detailed descriptions.

The focusing device provided by the present disclosure further includes a moving portion, configured to change a position of the X-ray beam to cause the X-ray beam to sequentially pass through the collimating channels of the same collimating channel group. That is, the X-ray beam sequentially passes through the collimating channels of the same collimating channel group, and the beam passing through each collimating channel group passes through the focus and focuses on the focus of the collimating channel group.

Figure 21:
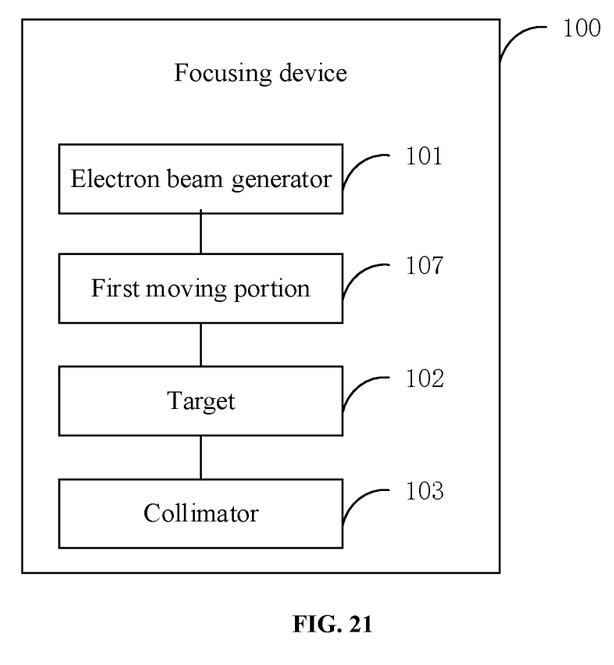
FIG. 21 is a schematic diagram of yet another focusing device in accordance with the present disclosure.

Exemplarily, the moving portion may move the X-ray beam horizontally or circumferentially. The moving portion may move the X-ray beam in various ways. Exemplarily, as shown in FIG. 21, a first moving portion 107 is included and configured to move the sub-electron beam, such that a shooting position of the sub-electron beam on the target changes, and the position of the X-ray beam changes as a result. Alternatively, a second moving portion 108 is further included and configured to horizontally move or circumferentially rotate the X-ray beam. That is, the X-ray beam is moved directly after the electron beam is shot onto the target to generate the X-ray beam. Certainly, the moving portion may be further configured to move the electron beam and the target, such that the position of the X-ray beam changes.

Figure 22:
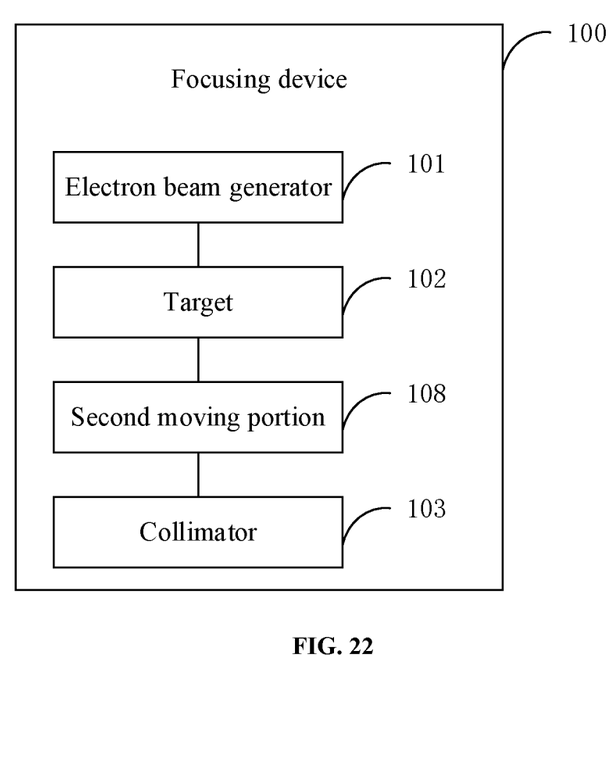
FIG. 22 is a schematic diagram of yet another focusing device in accordance with the present disclosure.

FIG. 21 and FIG. 22 show two different modes for the ray to sequentially pass through one or a plurality of collimating channels of the collimator. The ray passes through the focus o of the collimating channel group every time to focus on the focus o of the collimating channel group.

According to the focusing device provided by the present disclosure, the electron beam generator emits at least two electron beams. Referring to the embodiment shown in FIGS. 15 and 16 for details. Alternatively, the focusing device further includes a beam splitting component, configured to split the electron beam to form at least two sub-electron beams.

The present disclosure provides a radiotherapy apparatus, including any of the focusing devices provided by the present disclosure. It should be noted that the focusing device can realize a focused treatment of the radiotherapy apparatus. Certainly, the radiotherapy apparatus provided by the present disclosure may include a plurality of treatment heads, one of which is a focused treatment head. The focused treatment head may include any of the focusing devices provided by the present disclosure. The radiotherapy apparatus may also include a plurality of focused treatment heads, for example, two focused treatment heads, of which one is any of the focusing devices provided by the present disclosure and the other is a conventional Co-60 focused treatment head.

The radiotherapy apparatus provided by the present disclosure further includes at least one detector, configured to receive an X-ray beam. Exemplarily, the detector receives the X-ray beam and may verify a dose, a size, etc. of the X-ray beam to further adjust the X-ray beam, such that the X-ray beam meets the demands of a treatment plan.

The radiotherapy apparatus provided by the present disclosure further includes an imaging system. The imaging system includes a bulb tube and a flat panel detector. In the present disclosure, the radiotherapy apparatus may include one bulb tube and one flat panel detector, and may also include two bulb tubes and two flat-panel detectors.

The radiotherapy apparatus provided by the present disclosure further includes a conformal device. In the present disclosure, the conformal device is a device assembly for realizing the conformal treatment. The conformal device may be an accelerator treatment head and may also be a Co-60 treatment head. Exemplarily, a radioactive source, a multi-leaf collimator, etc. are included. The radioactive source may be a Co source and may also be an X-ray source. The radiotherapy apparatus provided by the present disclosure further includes a flat-panel detector configured to receive a radiation beam of the conformal device.

According to the radiotherapy apparatus provided by the present disclosure, the flat-panel detector may be moved to receive at least two of a beam of the bulb tube, the X-ray beam of the focusing device and a ray beam of the conformal device.

In the descriptions of the present disclosure, it is to be understood that orientation or positional relationships indicated by the terms "upper", "lower", "left", "right", etc. are orientation or positional relationships shown on the basis of the drawings, only for the purposes of the ease in describing the present disclosure and simplification of its descriptions, but not indicating or implying that the specified device or element has to be specifically located, and structured and operated in a specific direction, and therefore, should not be understood as limitations to the present disclosure. Moreover, the terms "first" and "second" are only for the purpose of description and should not be construed as indicating or implying relative importance or implicitly indicating the number of technical features indicated. Thus, the features defined by the terms "first" and "second" may include one or more of the features either explicitly or implicitly. In the descriptions of the present invention, unless otherwise stated, the term "plurality" means two or more. In addition, the term "comprise" and any of its variations are intended to cover a non-exclusive inclusion.

Described above are merely specific embodiments of the present disclosure, but the protection scope of the present disclosure is not limited thereto. Variation or substitutions that are readily conceivable by those skilled in the art within the technical scope of the present disclosure should fall within the protection scope of the present disclosure. Therefore, the protection scope of the present disclosure shall be subject to the protection scope defined by the claims.

What is claimed is:

1. A device for focusing an X-ray, comprising:
   an electron beam generator configured to emit an electron beam;
   a target;
   a collimator; and
   a moving portion,
   wherein the electron beam is capable of being shot on the target to generate an X-ray beam;
   wherein the collimator comprises at least one collimating channel group, each collimating channel group comprises at least two collimating channels, the collimating channels of different collimating channel groups are different in size, and the same collimating channel group has one focus or a plurality of focuses; and
   wherein the moving portion is configured to change a position of the X-ray beam to cause the X-ray beam to sequentially pass through the collimating channels of the same collimating channel group of the collimator.

2. The device for focusing an X-ray according to claim 1, wherein the moving portion moves the X-ray beam horizontally or circumferentially.

3. The device for focusing an X-ray according to claim 1, wherein the moving portion is configured to move the X-ray beam; or
   the moving portion is configured to move the electron beam to change a shooting position of the electron beam on the target and thus change the position of the X-ray beam; or
   the moving portion is configured to move the electron beam and the target and thus change the position of the X-ray beam.

4. The device for focusing an X-ray according to claim 1, wherein the electron beam generator emits at least two electron beams; or
   the focusing device further comprises a beam splitting component, configured to split the electron beam into at least two sub-electron beams.

5. The device for focusing an X-ray according to claim 4, wherein an incident extension line of the electron beam during target shooting forms an angle ranging from 0 to 90° with a central axis of the collimating channel.

6. The device for focusing an X-ray according to claim 1, wherein the electron beam is a divergent beam; or
   the electron beam generator emits a first electron beam; the focusing device further comprises a diverging component, configured to diverge the first electron beam to form a second electron beam; and the second electron beam is a divergent beam.

7. The device for focusing an X-ray according to claim 1, further comprising a flattening filter, wherein
the flattening filter is disposed between the electron beam generator and the target and configured to balance energy of the electron beam, such that energy of a contact surface between the electron beam and the target is balanced; or
the flattening filter is disposed between the target and the collimator and configured to balance energy of the X-ray beam.

8. The device for focusing an X-ray according to claim 1, wherein the same collimating channel group has one focus, and a focus position of the X-ray beam passing through the different collimating channel groups is same; or
the same collimating channel group has a plurality of focuses, and a plurality of focus positions of the X-ray beam passing through the same collimating channel group are different.

9. A radiotherapy apparatus, comprising at least one of a plurality of treatment heads, at least one detector, an imaging system, or a conformal device, and further comprising a device for focusing an X-ray,
wherein the device for focusing an X-ray comprises:
an electron beam generator, configured to emit an electron beam;
a target;
a collimator; and
a moving portion,
wherein the electron beam is shot on the target and an X-ray beam may be generated;
wherein the collimator comprises at least one collimating channel group, each collimating channel group comprises at least two collimating channels, the collimating channels of different collimating channel groups are different in size, and the same collimating channel group has one focus or a plurality of focuses; and
wherein the moving portion is configured to change a position of the X-ray beam to cause the X-ray beam to sequentially pass through the collimating channels of the same collimating channel group of the collimator.

10. The radiotherapy apparatus according to claim 9, wherein the moving portion moves the X-ray beam horizontally or circumferentially.

11. The radiotherapy apparatus according to claim 9, wherein the moving portion is configured to move the X-ray beam; or
the moving portion is configured to move the electron beam to change a shooting position of the electron beam on the target and thus change the position of the X-ray beam; or
the moving portion is configured to move the electron beam and the target and thus change the position of the X-ray beam.

12. A method for focusing an X-ray, comprising:
emitting an electron beam by an electron beam generator;
shooting the electron beam onto a target to generate an X-ray beam; and
causing the X-ray beam to pass through each collimating channel of a same collimating channel group of a collimator to focus on a focus of the collimating channel group, wherein the collimator comprises at least one collimating channel group; each collimating channel group comprises at least, two collimating channels; the collimating channels of different collimating channel groups are different in size; and the same collimating channel group has one focus or a plurality of focuses,
wherein the causing the X-ray beam to pass through each collimating channel of the same collimating channel group of the collimator comprises:
causing the X-ray beam to sequentially pass through collimating channels of the same collimating channel group of the collimator.

13. The method for focusing an X-ray according to claim 12, wherein the electron beam generator emits one electron beam; and
the shooting the electron beam onto a target to generate an X-ray beam comprises: shooting the one electron beam onto a target to emit one X-ray beam.

14. The method for focusing an X-ray according to claim 12, wherein the electron beam generator emits at least two electron beams;
the shooting the electron beam onto a target to generate an X-ray beam comprises: shooting the at least two electron beams onto a target to generate one X-ray beam respectively; and
the causing the X-ray beam to sequentially pass through each collimating channel of the same collimating channel group of a collimator comprises: causing each X-ray beam to pass through each collimating channel of the same collimating channel group of a collimator and to focus on a focus of the collimating channel group.

15. The method for focusing an X-ray according to claim 14, wherein focus positions of the X-ray beams are the same.

16. The method for focusing an X-ray according to claim 12, wherein the X-ray beam moves circumferentially or horizontally and sequentially passes through each collimating channel of a same collimating channel of a collimator.

17. The method for focusing an X-ray according to claim 12, wherein the shooting the electron beam onto a target to generate an X-ray beam comprises:
moving the electron beam to change a shooting position of the electron beam on the target and to respectively generate an X-ray beam at each shooting position of the target.

18. The method for focusing an X-ray according to claim 12, wherein before shooting the electron beam onto a target to generate an X-ray beam, the method further comprises:
splitting the electron beam into at least two sub electron beams;
the shooting the electron beam onto a target to generate an X-ray beam comprises: shooting the at least two sub-electron beams onto a target to generate one X-ray beam respectively; and
the causing the X-ray beam to pass through each collimating channel of the same collimating channel group of a collimator to focus on a focus of the collimating channel group comprises: causing each X-ray beam to pass through or sequentially pass through each collimating channel of the same collimating channel group of a collimator to focus on a focus of the collimating channel group.

19. The method for focusing an X-ray according to claim 12, wherein the electron beam is a divergent beam; or
the electron beam generator emits a first electron beam; and
before shooting the first electron beam onto a target to generate an X-ray beam, the method further comprises:
diverging the first electron beam to form a second electron beam, wherein the second electron beam is a divergent beam.

20. The method for focusing an X-ray according to claim 12, further comprising:
    balancing energy of the electron beam to cause energy of a contact surface between the electron beam and the target to be balanced; or
    balancing energy of the X-ray beam.

* * * * *